(12) United States Patent
Lang et al.

(10) Patent No.: US 6,388,073 B1
(45) Date of Patent: May 14, 2002

(54) METHOD FOR THE MANUFACTURE OF ANAGRELIDE

(75) Inventors: Philip C. Lang, Toms River; Roxanne P. Spencer, Plainsboro, both of NJ (US); Wen-Lung Yeh, Thornhill; Michael Joseph Roth, Bolton, both of (CA)

(73) Assignee: Shire US Inc., Florence, KY (US)

( * ) Notice: Subject to any disclaimer, the term of this patent is extended or adjusted under 35 U.S.C. 154(b) by 0 days.

(21) Appl. No.: 09/625,962

(22) Filed: Jul. 26, 2000

(51) Int. Cl.$^7$ .............................................. C07D 487/04

(52) U.S. Cl. ....................................................... 544/250

(58) Field of Search ......................................... 544/250

(56) References Cited

U.S. PATENT DOCUMENTS

| | | | |
|---|---|---|---|
| 3,932,407 A | 1/1976 | Beverung, Jr. et al. | 260/251 |
| 4,146,718 A | 3/1979 | Jenks et al. | 544/492 |
| 4,208,521 A | 6/1980 | Crenshaw et al. | 544/250 |
| 4,357,330 A | 11/1982 | Fleming, Jr. et al. | 424/232 |
| RE31,617 E | 6/1984 | Beverung, Jr. et al. | 544/250 |
| 4,808,405 A | 2/1989 | Smith et al. | 424/94.3 |
| 5,334,384 A | 8/1994 | Mannix et al. | 424/94.3 |
| 5,801,245 A | 9/1998 | Lang | 544/250 |

*Primary Examiner*—John M. Ford
(74) *Attorney, Agent, or Firm*—DeLio & Peterson, LLC

(57) ABSTRACT

Methods are provided for making Anagrelide base from 2,3-dichlorobenzaldehyde. A method is also provided for making an intermediate compound ethyl N-(2,3-dichloro-6-nitrobenzyl)glycine from 2,3-dichlorobenzaldehyde and for reducing the glycine compound using either $SnCl_2$ or a specially defined catalyst. A cyclization method to form Anagrelide base from the corresponding iminoquinazoline compound is further provided.

2 Claims, No Drawings

METHOD FOR THE MANUFACTURE OF ANAGRELIDE

BACKGROUND OF THE INVENTION

1. Field of the Invention

The invention relates to 6,7-dichloro-1,5-dihydroimidazo[2,1-b]quinazolin-2(3H)-one (compound III), more commonly known as Anagrelide base and, more particularly, to a method for the manufacture of Anagrelide base.

2. Description of Related Art

Anagrelide (6,7-dichloro-1,5-dihydroimidazo[2,1-b]quinazolin-2(3H)-one, (compound III) is a potent blood platelet reducing agent. A number of U.S. Patents have issued on Anagrelide and its method of making including U.S. Pat. Nos. 3,932,407; 4,146,718; 4,208,521; 4,357,330; Re 31,617; and 5,801,245. These patents are incorporated herein by reference.

Commercially, as discussed in U.S. Pat. No. 5,801,245 and as shown in FIG. 1, Anagrelide has been prepared as the hydrochloride monohydrate (compound IV) from the intermediate, ethyl N-(6-amino-2,3-dichlorobenzyl)glycine (compound I) by reaction with cyanogen bromide in hot alcohol solution, or, preferentially, by reaction with cyanogen bromide in an aprotic solvent to give the iminoquinazoline intermediate (compound II) which is isolated and then reacted with a base in a hot solution of alcohol to form Anagrelide base (compound III).

FIG. 1

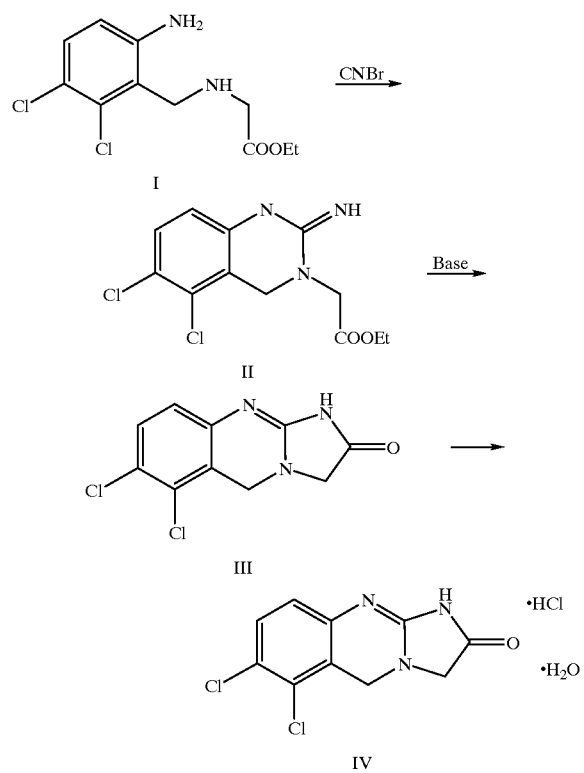

The hydrochloride monohydrate Anagrelide salt (compound IV) is prepared by adding hydrochloric acid to a methanol slurry of Anagrelide base (compound III) and heating to reflux. The hydrochloride salt is then hydrated in a high humidity chamber. These two steps are time-consuming however, and the yield of hydrochloride salt can be poor due to competing acid hydrolysis of the lactam ring and methyl ester formation. After 15 minutes at reflux, the isolated yield is 62% and this decreases to 40% after 2 hours.

Normally, salts are prepared when the free base has undesirable properties such as poor solubility or a non-solid physical state. In this case, both Anagrelide base (compound III) and the hydrochloride salt (compound IV) are solids with low aqueous solubility. In addition, the water of crystallization can accelerate decomposition of the parent molecule through hydrolysis of the lactam ring and this presents long-term stability problems for pharmaceutical Anagrelide formulations.

Radiolabeled Anagrelide base has been used in pharmacokinetic studies in humans and monkeys and results show complete absorption into blood plasma demonstrating that the base is bioavailable. The free-base is converted into the hydrochloride salt in the stomach to enhance absorption. Both the salt and the base exhibit equivalent pharmacological effects, and there is no inherent advantage to using the hydrochloride monohydrate salt as the active pharmaceutical agent.

As an important intermediate in the synthesis of Anagrelide, ethyl N-(6-amino-2,3-dichlorobenzyl)glycine (compound I) has been prepared from 2,3-dichloro-6-nitrobenzylamine (compound V) as shown in FIG. 2. This material is no longer commercially readily available, however, as the precursor 2,3-dichloro-6-nitrobenzonitrile has extreme toxic and skin-irritant properties.

FIG. 2

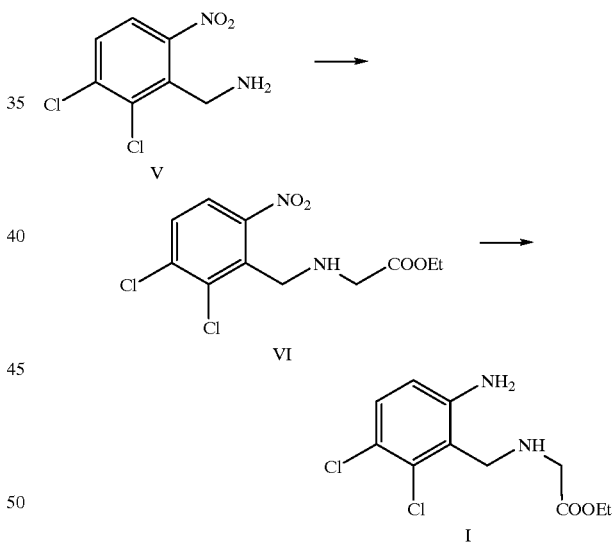

The conventional process for the formation of ethyl N-(6-amino-2,3-dichlorobenzyl)glycine (compound 1) from 1,2,3-trichlorobenzene is shown in U.S. Pat. No. 4,146,718.

An improved process for the formation of ethyl-N-(6-amino-2,3-dichlorobenzyl)glycine (compound 1) involving the intermediate 2,3-dichloro-6-nitrobenzyl halide (compound VIII), where halide is iodide, chloride or bromide, has been developed as an environmentally acceptable alternative (FIG. 3). The route of preparation from 2,3-dichloro-6-nitro-toluene (compound VII) is claimed in U.S. Pat. No. 5,801,245, and involves a radical halogenation of the toluene group. Radical conditions can be nonselective, however, and could be difficult to effectively implement in large-scale commercial manufacture.

FIG. 3

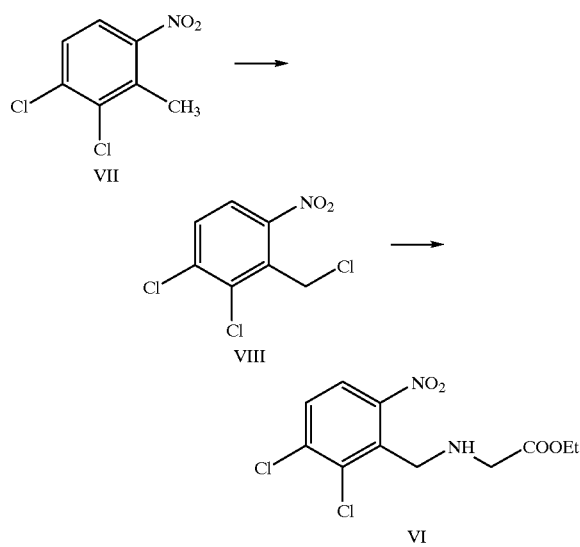

FIG. 4

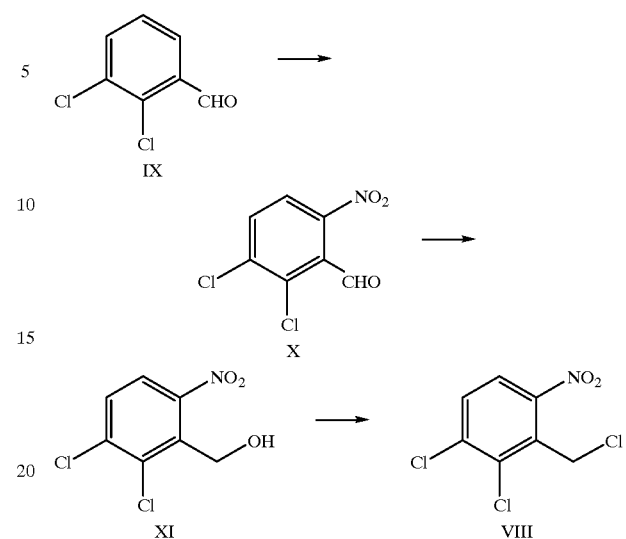

In both reactions shown in FIGS. 2 and 3, ethyl N-(2,3-dichloro-6-nitrobenzyl)glycine (compound VI) is reduced to the 6-amino-2,3-dichlorobenzyl glycine (compound I) by stannous chloride reduction ($SnCl_2$/HCl). A disadvantage of this route is the formation of large amounts of tin-containing waste products. In addition, the strongly acidic reaction conditions can promote chlorination of the aromatic ring, producing a mixture of tri-chloro impurities which are difficult to remove in successive steps.

Bearing in mind the problems and deficiencies of the prior art, it is therefore an object of the present invention to provide a method for the making of Anagrelide HCl (compound IV) and Anagrelide base (compound III).

It is an additional method of the present invention to make intermediate 2,3-dichloro-6-nitrobenzyl chloride (compound VIII) from readily available starting materials.

It is another object of the present invention to provide a method for making intermediate ethyl-(6-amino-2,3-dichlorobenzyl)glycine (compound I) from ethyl N-(2,3-dichloro-6-nitrobenzyl)glycine (compound VI) using either $SnCl_2$ or a hydrogenation catalyst as the reducing agent.

A further object of the present invention is to provide a method for the cyclization of 5,6-dichloro-3,4-dihydro-2 (1H)iminoquinazoline-3-acetate HBR (compound II) to form Anagrelide base (compound III).

Still other objects and advantages of the present invention will in part be obvious and will in part be apparent from the specification.

SUMMARY OF THE INVENTION

The above and other objects, which will be apparent to those skilled in the art, are achieved by the present invention which relates in a first aspect to an environmentally acceptable method for making the intermediate 2,3-dichloro-6-nitrobenzyl chloride (compound VIII) from readily available starting materials (FIG. 4). As shown in FIG. 4, 2,3-dichlorobenzaldehyde (compound IX) is nitrated preferentially at the 6-position to form 2,3-dichloro-6-nitro benzaldehyde (compound X), separated from its isomer, and reduced to 2,3-dichloro-6-nitrobenzyl alcohol (compound XI) under standard hydride conditions. Treatment of the alcohol under standard nucleophilic displacement conditions gives 2,3-dichloro-6-nitrobenzyl chloride (compound VIII).

The above compounds can also contain substituents such as F,Cl, Br and I and the like. Further, the 2,3 chlorine atoms may likewise be substituted with substituents such as F, Br and I. This will also apply to the other reaction schemes shown hereinbelow and for convenience the description will be directed to the desired unsubstituted dichloro compounds.

Ethyl N-(2,3-dichloro-6-nitrobenzyl)glycine (compound VI) is then produced by reaction of 2,3-dichloro-6-nitrobenzyl chloride (compound VIII) with ethyl glycine, compound VI reduced to form compound I which is reacted to form compound II and then cyclized to form Anagrelide base (compound III) as shown below:

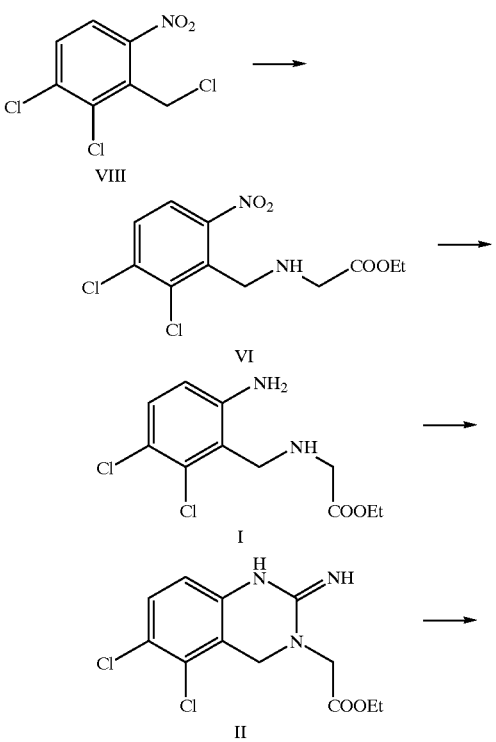

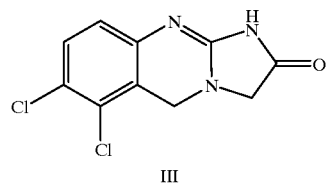

III

Alternatively, compound VI can be made directly from 2,3-dichloro-6-nitro benzaldehyde (compound X) by reductive amination with a glycine ester as shown in FIG. 5. This is a novel approach to the known intermediate compound VI, which intermediate is reduced to compound I by either catalytic hydrogenation or by stannous chloride preferably following the method of the invention.

FIG. 5

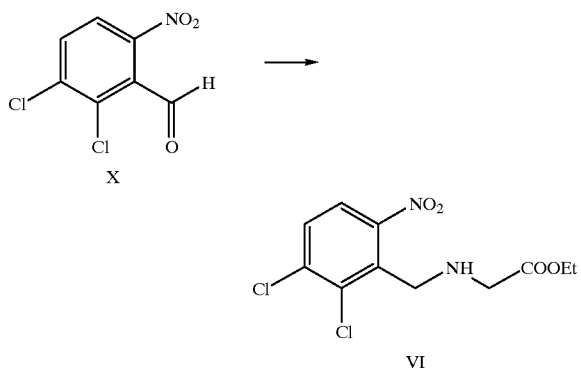

Normally, catalytic hydrogenation of aromatic chloro compounds such as ethyl N-(2,3-dichloro-6-nitrobenzyl) glycine (compound VI) is accompanied by excessive dechlorination, however, it has been found that a specially defined poisoned catalyst (for example, sulfided platinum on a carbon support) allows the selective reduction of the nitro group without significant chlorine loss at moderate hydrogen pressures. Other catalysts include Raney nikel, rhodium or palladium on a carbon support. This is an environmentally acceptable alternative to the tin-acid reductions conventionally used in the preparation of Anagrelide since the heterogeneous poisoned catalyst can be recycled. This novel method eliminates the production of large quantities of tin-containing waste of the prior art and produces material in higher yield and purity than the conventional route. Though this selective catalytic hydrogenation is preferable, this invention also includes, in another aspect an improved reduction reaction under stannous chloride/acid conditions that allows control of trichloro impurities.

Another aspect of the invention for the preparation of Anagrelide is the discovery that the final cyclization reaction as shown for example in FIG. 1 to form 6,7-dichloro-1,5-dihydroimidazo[2,1-b]quinazoline-2(3H)one (compound III) from 5,6-dichloro-3,4-dihydro-2(1H)iminoquinazoline-3-acetate HBR (compound II) can be achieved at room temperature by addition of an organic base such as triethylamine (TEA), pyridine, or trimethylamine, preferably TEA, to a suspension of the starting material in water. Anagrelide base is obtained in about 99.8% purity by HPLC. The preparation of Anagrelide base from ethyl 5,6-dichloro-3,4-dihydro-2(1H)iminoquinazoline-3-acetate hydrobromide (compound II) is conventionally achieved by cyclization in refluxing organic alcohols in the presence of a base. This leads to occlusion of residual solvents or organic impurities in the final product. Due to the low solubility of Anagrelide free base in most organic solvents, further purification at this stage is limited. Since the iminoquinazoline intermediate 5,6-dichloro-3,4-dihydro-2(1H)iminoquinazoline-3-acetate HBR (compound II) is insoluble in water at room temperature, the discovery that this media affords much purer Anagrelide base (compound III) is surprising and novel.

The formation of the Anagrelide hydrochloride salt in refluxing methanol/hydrochloric acid possesses a powerful purification effect, readily removing the organic and solvent impurities. However, at reflux conditions, acid hydrolysis is fast and the yield of hydrochloride salt decreases rapidly over time. With the larger batch sizes needed for commercial manufacture, the time the reaction mixture spends at reflux is significant. Thus, formation of the hydrochloride salt is a less efficient means of purification than preparing Anagrelide base (compound III) in high purity using the method of the invention.

DESCRIPTION OF THE PREFERRED EMBODIMENTS

The nitration of 2,3-dichlorobenzaldehyde (compound IX) to form 2,3-dichloro-6-nitro benzaldehyde (compound X) is performed preferably by adding concentrated nitric acid to a solution of compound IX in sulfuric acid using an ice bath to maintain a reaction temperature of about −10 to 40° C., preferably 20–25° C. The reaction mixture is generally stirred at this temperature for one hour or more and then preferably suspended in water and filtered. The filter cake is preferably washed with water to give a mixture of the compound X and its isomer 5-nitrobenzaldehyde. The isomers may be separated using an organic solvent such as hexane until the 5-nitro isomer is removed.

To form 2,3dichloro-6-nitro benzylalcohol (compound XI) from 2,3-dichloro-6-nitro benzaldehyde (compound X), compound X is preferably solubilized in a solvent such as toluene and methanol. The solution of compound X is added to a reducing solution such as sodium borohydride in an organic solvent over a period of time to maintain a reaction temperature below about 40° C., preferably 25° C. The reaction is preferably stirred for 24 hours at room temperature under nitrogen and then washed with water. After removing the aqueous layer the organic layer is azeotropically dried and concentrated forming 2,3dichloro-6-nitro benzylalcohol (compound XI).

To form 2,3-dichloro-6-nitrobenzyl chloride (compound VIII) from 2,3dichloro-6-nitro benzylalcohol (compound XI) a concentrated solution of compound XI is preferably prepared and a base such as triethylamine is added to the concentrated solution. To this solution is added a chlorinating material, preferably thionyl chloride, over about 15 minutes. Following addition, the solution is heated for a number of hours such as 45–50° C. for 18 hours and then cooled to room temperature. Water and organic solvents such as toluene are added to the reaction mixture and the mixture filtered. The organic layer is washed with water and dried by azeotropic distillation and the solution concentrated to give 2,3-dichloro-6-nitrobenzyl chloride (compound VIII).

Ethyl N-(2,3-dichloro-6-nitrobenzyl)glycine (compound VI) is formed from 2,3-dichloro-6-nitrobenzyl chloride (compound VIII) by preferably reacting under nitrogen an organic base such as triethylamine, a glycine ethylester and a phase transfer castalyst such as cetyltrimethyl ammonium bromide at an elevated temperature such as 80° C. for 24 hours. To the cooled mixture is added a salt solution such as sodium chloride and the organic phase separated, washed with water and concentrated. The salt ethyl N-(2,3-dichloro-6-nitrobenzyl)glycine (compound VI) is prepared by treating the crude material with HCl and isopropanol and filtering the precipitate.

Ethyl N-(2,3-dichloro-6-nitrobenzyl)glycine (compound VI) is preferably prepared by reductive amination of 2,3-dichloro-6-nitrobenzaldehyde (compound X) with a mixture of TEA and an alcohol. A reducing agent such as sodium cyanoborohydride is added in small portions and reaction mixture stirred. The product is isolated by filtration.

Ethyl-(6-amino-2,3-dichlorobenzyl)glycine (compound I) is preferably prepared from ethyl N-(2,3-dichloro-6-nitrobenzyl)glycine (compound VI) using a mixture of stannous chloride and hydrochloric acid following the method of the invention. A solution of ethyl N-(2,3-dichloro-6-nitrobenzyl)glycine (compound VI) is slowly added to the tin solution and the resulting reaction mixture heated at an elevated temperature of about 40–50° C. for about two hours. Solids are filtered and the filtered cake dissolved in water and an organic solvent such as methylene chloride. The pH of the solution is adjusted to about 12.5 with sodium hydroxide and the organic phase separated and the aqueous phase extracted with methylene chloride. The combined organic phases are washed with water and dried azeotropically and the solution is concentrated, an organic solvent added and the solution cooled to −20 to −30° C. The precipitated solids are collected by filtration and the crude product is recrystallized from heptane or another organic solvent.

Ethyl N-(2,3-dichloro-6-nitrobenzyl)glycine (compound VI) may also be catalytically hydrogenated using a sulfided platinum on carbon catalyst under hydrogen pressure. The catalyst is then removed by filtration and the filtrate concentrated, diluted with water and an organic solvent and basified using an alkali to a pH of about 9–10. The organic phase is separated and concentrated and the crude material purified by low temperature recrystallization to give ethyl-(6-amino-2,3-dichlorobenzyl)glycine (compound I).

6,7-dichloro-1,5-dihydroimidazo[2,1-b]quinazoline-2 (3H)one (compound III) may be prepared from compound II by suspending 5,6-dichloro-3,4-dihydro-2(1H) iminoquinazoline-3-acetate HBR (compound II) in water and adding an organic base such as TEA. After filtering the solution the filtered cake is washed in water and the solids suspended in alcohol. After filtering, the solids are rinsed in an alcohol and dried to give compound III.

EXAMPLES

Preparation of 2,3-Dichloro-6-nitrobenzaldehyde (X)

A solution of 40 g of 2,3-dichlorobenzaldehyde (compound IX) in 160 mL of concentrated sulfuric acid (95–98% w/w) is heated to 40° C. and stirred to form a solution, then cooled to 20–25° C. Concentrated nitric acid (69–71 % w/w; 24.7 g) is added to this solution over 20 minutes (an ice bath is used to maintain a reaction temperature of 20–30° C.). The reaction mixture is stirred at room temperature for 1 hour, and then added in portions to 600 mL of water. The resulting suspension is stirred for 2 hours and filtered. The filter cake is washed (3×50 mL of water). The filter cake is agitated with 200 mL of water for 2 hours and filtered. The filter cake is washed (3×50 mL of water) and dried in vacuo to give a mixture of the compound X and the isomer, 2,3-dichloro-5-nitrobenzaldehyde.

The crude product is triturated with hexanes for 3 hours and filtered. The filter cake is washed with hexanes (2×70 mL). This trituration procedure is repeated with fresh hexanes until the 5-nitro isomer is removed. The filter cake is then dried in vacuo to give the purified compound X in 44 to 50% yield.

$^1$H NMR(CDCl$_3$, 300 MHz): δ7.8(d, 1H); 8.0 (d, 1H); 10.4 (s, 1H)

Preparation of 2,3-Dichloro-6-nitrobenzylalcohol (XI)

A solution of 40 g of 2,3-dichloro-6-nitrobenzaldehyde (compound X) in 200 mL of toluene was stirred for five minutes. Then, 7.4 mL of methanol was added and mixing continued until all the solids had dissolved. Separately, a solution of 2.41 g of sodium borohydride in 120 mL of toluene was prepared. The benzaldehyde solution was added by drops to the borohydride solution over 20 minutes to maintain the reaction temperature below 25° C. The reaction mixture was stirred for 24 hours at room temperature under nitrogen. Forty mL of water was added and the mixture stirred for 15 minutes. The aqueous layer was removed and the organic layer washed with water (3×40 mL). The organic layer was azeotropically dried using a Dean-Stark trap, and concentrated to 280 mL. The 2,3-dichloro-6-nitrobenzylalcohol (compound XI) was used without further purification.

$^1$H NMR (CDCl$_3$, 300 MHz): δ7.8 (d, 1H); 7.6 (d, 1H); 5.0 (s, 2H)

Preparation of 2,3-dichloro-6-nitrobenzyl chloride (VIII)

Under nitrogen, 27.9 mL of triethylamine was added to the concentrated solution of 2,3-dichloro-6-nitrobenzylalcohol (compound XI) prepared in the previous step. To this solution, 14.6 mL of thionyl chloride was added via an addition funnel over 15 minutes. Following addition, the solution is heated to 45–50° C. for 18 hours, then cooled to room temperature under nitrogen. Water and toluene are added to the reaction mixture and the mixture filtered. The filtrate is diluted with water, and the aqueous layer removed. The organic layer is washed with water (4×40 mL), and dried by azeotropic distillation. The solution is concentrated to give 1,2-dichloro-3-chloromethyl-4-nitrobenzene (compound (VIII), which could be used without further purification.

$^1$H NMR (CDCl$_3$, 300 MHz): δ7.8 (d, 1H); 7.6 (d, 1H); 5.0 (s, 2H)

Preparation of Ethyl N-(2,3-dichloro-6-nitrobenzyl) glycine hydrochloride (VI)

A. Alkylation

Under nitrogen, 47.5 mL of triethylamine, 25.9 g of glycine ethyl ester hydrochloride and 2.8 g of cetyltrimethylammonium bromide is added to the toluene solution of 1,2-dichloro-3-chloromethyl-4-nitrobenzene (compound VIII) prepared in the previous step. The reaction mixture is heated at 80° C. for 24 hours. To the cooled mixture is added 40 mL of 20% NaCl solution. The organic phase is separated, washed with water, and concentrated. The salt (compound VI) is prepared in 66 to 71% yield by treating the crude material with HCl in isopropanol and filtering the precipitate.

B. Reductive Amination

The compound (VI) can be prepared by reductive amination of 2,3-dichloro-6-nitrobenzaldehyde (compound X) with 1.1 equivalents of glycine ethyl ester hydrochloride in a mixture of anhydrous triethylamine over KOH and 95:5% mixture of ethanol and isopropanol. Sodium cyanoborohydride (2.5 equivalents) is added in small portions and the reaction mixture stirred for 16 hours. The product is isolated by filtration. The filtrate is concentrated, dissolved in ethyl acetate and washed with saturated aqueous sodium chloride solution. The organic base is extracted (2 N HCl,4x), the aqueous phases combined and neutralized with saturated aqueous potassium carbonate. The aqueous phase is next extracted with ethyl acetate. The organic phases are combined, washed with saturated aqueous sodium chloride solution, dried (sodium sulfate) and concentrated to give the product in 60% yield.

$^1$H NMR (300 MHZ, DMSO-d$_6$): δ9.89 (br s, NH); 8.23 (d, 1H, J=9.2 Hz, C(2)-H); 8.08 (d, 1H, J=8.8 Hz, C(3)-H); 4.69 (s, 2H, C(7)-H$_2$); 4.23 (q, J=7 Hz, 2H, C(10)-H$_2$); 4.12 (s, 2H, C(8)-H$_2$); 1.26 (t, J=7 Hz, 3H, CH$_3$)

$^{13}$C NMR (75 MHz, DMSO-d6): δ13.90 (C11); 44.86 (C7); 47.74 (C8); 125.06 (C2); 127.72 (C6); 132.90 (C3); 135.65 (C5); 137.99 (C4); 149.11 (C1); 166.43 (C9)

UV: 214 nm (Σ=18447 M$^{-1}$cm$^{-1}$); 266 nm (Σ=7054 M$^{-1}$cm$^{-1}$); 328 nm (Σ=1593 M$^{-1}$cm$^{-1}$)

MS: 307 (M$^+$)

IR (KBr dispersion): 1750 cm$^{-1}$ (C=O); 1520 (NO$_2$); 1350 (NO$_2$) 1210 (C—O); 875 (C—N)

Preparation of Ethyl N-(6-amino-2,3-dichlorobenzyl)glycine (I)

A. SnCl$_2$ Reduction

A suspension of 30 g of ethyl N-(2,3-dichloro-6-nitrobenzyl)glycine hydrochloride (compound VI) in 120 mL of concentrated hydrochloric acid was prepared. Separately, a mixture of tin chloride dihydrate (88.6 g) in 60 mL of hydrochloric acid is prepared. The glycine solution is slowly added to the tin solution and the resulting reaction mixture heated for 2 hours at 40–50° C. The solids are filtered, and the filter cake dissolved in water and methylene chloride. The pH of this solution is adjusted to 12.5 with 50% NaOH. The organic phase is separated and the aqueous phase extracted with methylene chloride. The combined organic phases are washed with water, and dried azeotropically. The solution is concentrated, isopropanol and heptane are added, and the solution cooled to −20 to −30° C. The precipated solids are collected by filtration. The crude product is recrystallized from heptane to give compound I in 58 to 67% yield.

B. Catalytic Hydrogenation

A solution of 0.344 g of ethyl N-(2,3-dichloro-6-nitrobenzyl)glycine hydrochloride (compound VI) in 1.5 mL of water and 1.5 mL ethanol (with 5% isopropanol) was stirred and 5% sulfided platinum on carbon under hydrogen (50 to 100 psi) for 16 hours. The catalyst was removed by filtration. The filtrate concentrated, diluted with water and toluene, and basified (aqueous sodium hydroxide or potassium carbonate) to pH 9–10. The organic phase was separated, concentrated, and the crude material purified by low-temperature recrystallization from toluene in hexane to give compound I in 72% yield.

$^1$H NMR (300 MHz, DMSO-d$_6$): δ7.18 (d, 1H, J=8.8 Hz); 6.64 (d, 1H, J=8.8 Hz); 5.74 (s, 2H); 4.11 (q, 2H, J=7.35 Hz); 3.84 (s, 2H); 3.34 (s, 2H); 1.21 (t, J=7.35 Hz, 3H)

$^{13}$C NMR (75 MHz, DMSO-d$_6$): δ14.12 (C11); 46.63 (C8); 49.01 (C7); 60.12 (C10); 114.51 (C2); 117.39 (C4); 121.65 (C6); 129.0 (C3); 131.46 (C5); 148.40 (C1); 172.34 (C9)

UV: 210 nm (Σ=38378 M$^{-1}$ cm$^{-1}$); 251 nm (Σ=13254 M$^{-1}$ cm$^{-1}$); 307 nm (Σ=3368 M$^{-1}$ cm$^{-1}$)

MS: 277 (M$^+$); 176 (M$^+$-C$_4$H$_9$NO$_2$); 116 (M$^+$- C$_6$H$_4$NCl$_2$)

IR (KBr dispersion): 3420 cm$^{-1}$, 3300 (NH); 1730 (C=O); 1620 (NH); 1190 (C—O)

Preparation of 5,6-dichloro-3,4-dihydro-1(1H) iminoquinazoline-3 acetate hydrobromide (II)

Ethyl N-(6-amino-2,3-dichlorobenzyl)glycine was dissolved in 4 parts of toluene. A solution of cyanogen bromide (1.1 equivalent) in 4 parts of toluene was then added while maintaining the reaction mixture temperature below 30° C. The reaction mixture was heated to reflux for 1 hour. The mixture was cooled to 0–5° C. and stirred at 0–5° C. for 1 hour. The mixture was filtered and the solids were rinsed with toluene (2×1 part). The solids were dried at 50° C. in a high vacuum oven overnight to give Compound II in 96–98% yield.

$^1$H NMR (300 MHz, DMSO-d$_6$): δ7.57 (d, 1H, J=8.5 Hz); 7.05 (d, 1H, j=8.5 Hz); 4.67 (S, 2H); 4.55 (S, 2H); 4.19 (q, 2H, J=7.0 Hz); 1.25 (t, 3H, J=7.0 Hz)

$^{13}$C NMR (75 MHz, DMSO-d$_6$): δ14.15; 48.07; 50.46; 61.80; 115.05; 118.42; 126.22; 128.19; 129; 130.16; 132.92; 167.09

UV: 217 nm (Σ=40337 M$^{-1}$ cm$^{-1}$-); 262 nm (Σ=18961 N$^{-1}$cm$^{-1}$)MS: 302 (M$^1$-HBr); 256 (M$^+$-C$_2$H$_7$OBr)

IR: (KBr dispersion): 3200 cm$^{-1}$; 1740 (C=O); 1666 (C=N); 1200 (C—O).

Preparation of 6,7-Dichloro-1,5-dihydroimidazo[2, 1-b]quinazolin-2(3H)-one (III)

5,6-dichloro-3,4-dihydro-2(1H)iminoquinazoline-3-acetate HBR (compound II) was suspended in 46 parts water. TEA (1.5 equiv.) was added in one portion, and the mixture stirred for 2 hours. The solution was filtered, and the filter cake washed with water (2×3 parts). The solids were suspended in ethanol (20 parts) and stirred for 4 hours. The solution was filtered. The solids were rinsed with ethanol (2×⅔ parts), and dried at 40° C. in a high vacuum oven overnight to give compound III in 86 to 88% yield.

Melting point: 338–341° C.

$^1$H NMR (300 MHz, DMSO-d$_6$, TFA-d$_1$); δ13 (br s, NH); 7.15 (d, 1H, J=8.7 Hz, C(3)-H); 7.12 (d, 1H, J=8.7 Hz, C(2)-H); 4.71 (s, 2H, C(7)-H $_2$); 4.29 (s, 2H, C(8)-H$_2$)

$^{13}$C NMR (75 MHz, DMSO-d$_6$, TFA-d$_1$): δ44.01 (C7); 52.56 (C8); 117.10 (C2); 127.92 (C4); 129.58 (C6); 130.52 (C3); 132.11 (C5); 153.28 (C1); 171.34 (C9)

UV: 210 nm (Σ=18772 M$^{-1}$ cm$^{-1}$); 255 nm (Σ=22708 M$^{-1}$ cm$^{-1}$)

MS: 256 (M$^+$); 221 (M—Cl)

IR (KBr dispersion): 3010, 3000, 1700 (C=O), 1630 (C=N), 1562, 1468, 1437(C=C), 1197, 1187 cm$^{-1}$ While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. A method for making Anagrelide base 6,7-dichloro-1, 5-dihydroimidazo[2,1-b]quinazoline-2(3H)one (compound III) from 2,3-dichlorobenzaldehyde (compound IX) comprising the steps:

(a) nitrating a compound IX of the formula:

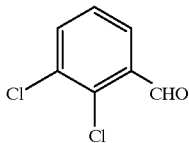

IX to form compound X of the formula:

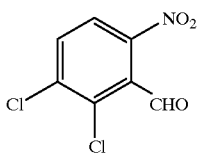

X (b) reacting compound X under reducing conditions to form compound XI of the formula:

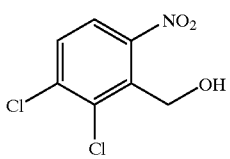

XI (c) reacting compound XI under chlorination conditions to form compound VIII of the formula:

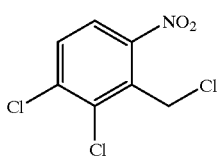

VIII (d) reacting compound VIII under alkylation conditions to form compound VI of the formula:

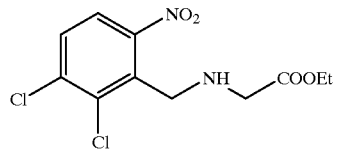

VI (e) reacting compound VI under reducing conditions to form compound I of the formula:

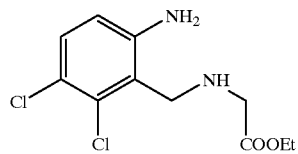

I (f) reacting compound I under bromocyanation conditions to form compound II of the formula:

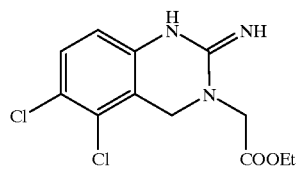

II (g) reacting compound II under cycloalkylation conditions to form compound III of the formula:

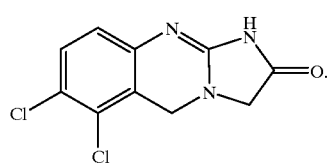

III

2. A method for the cyclization of 5,6-dichloro-3,4-dihydro-2(1H)iminoquinazoline-3-acetate HBR (compound II) to form 6,7-dichloro-1,5-dihydroimidazo[2,1-b]quinazolin-2(3H)-one (compound III) comprising the steps of:
   suspending the iminoquinazoline salt in water;
   adding an organic base to the suspension and mixing; and
   separating and drying the solids to form 6,7-dichloro-1,5-dihydroimidazo[2,1-b]quinazolin-2(3H)-one.

* * * * *